(12) United States Patent
Armitage et al.

(10) Patent No.: US 8,956,588 B2
(45) Date of Patent: Feb. 17, 2015

(54) SELECTIVE DEALUMINATION OF MOR TYPE ZEOLITES

(75) Inventors: Gareth Gerald Armitage, York (GB); John Glenn Sunley, Cottingham (GB)

(73) Assignee: BP Chemicals Limited, Middlesex (GB)

( * ) Notice: Subject to any disclaimer, the term of this patent is extended or adjusted under 35 U.S.C. 154(b) by 468 days.

(21) Appl. No.: 12/998,348

(22) PCT Filed: Sep. 29, 2009

(86) PCT No.: PCT/GB2009/002293
§ 371 (c)(1),
(2), (4) Date: Aug. 24, 2011

(87) PCT Pub. No.: WO2010/043843
PCT Pub. Date: Apr. 22, 2010

(65) Prior Publication Data
US 2011/0306785 A1 Dec. 15, 2011

(30) Foreign Application Priority Data

Oct. 13, 2008 (EP) ..................................... 08253328

(51) Int. Cl.
| | | |
|---|---|---|
| *C01B 33/36* | (2006.01) | |
| *C07C 67/36* | (2006.01) | |
| *C07C 53/08* | (2006.01) | |
| *B01J 37/00* | (2006.01) | |
| *B01J 29/18* | (2006.01) | |
| *B01J 29/22* | (2006.01) | |
| *B01J 35/02* | (2006.01) | |
| *B01J 37/10* | (2006.01) | |
| *C07C 51/09* | (2006.01) | |
| *C07C 51/12* | (2006.01) | |
| *C07C 67/37* | (2006.01) | |

(52) U.S. Cl.
CPC .............. *B01J 37/0009* (2013.01); *B01J 29/18* (2013.01); *B01J 29/22* (2013.01); *B01J 35/023* (2013.01); *B01J 37/10* (2013.01); *C07C 51/09* (2013.01); *C07C 51/12* (2013.01); *C07C 67/36* (2013.01); *C07C 67/37* (2013.01); *B01J 2229/16* (2013.01); *B01J 2229/36* (2013.01); *B01J 2229/37* (2013.01)
USPC ............................ 423/700; 560/232; 562/607

(58) Field of Classification Search
CPC ........ B01J 29/19; B01J 29/22; B01J 37/0009; B01J 37/10; C07C 51/09; C07C 51/12; C07C 67/36; C07C 67/37
USPC ............................ 560/232; 562/607; 423/700
See application file for complete search history.

(56) References Cited

U.S. PATENT DOCUMENTS

| | | | | |
|---|---|---|---|---|
| 4,151,120 | A * | 4/1979 | Marcilly | ........................ 502/74 |
| 4,654,316 | A * | 3/1987 | Barri et al. | ...................... 502/61 |
| 4,902,847 | A | 2/1990 | Juguin et al. | |
| 6,486,372 | B1 * | 11/2002 | Merlen et al. | ................. 585/467 |

FOREIGN PATENT DOCUMENTS

WO   WO2005105720   *   4/2004   .............. C07C 51/12

OTHER PUBLICATIONS

Bhan et al., Specificity of Sites within Eight-Membered Ring Zeolite Channels for Carbonylation of Methyls to Acetyls, Journal of the American Chemical Society, 129, 4919-4924 (2007).*
Mohamed, Structural and acidic characteristics of Cu-Ni-modified acid-leached mordenites, Journal of Colloid and Interface Sciences, 265, 106-114 (2003).*
Mohamed et al., Characterization of Gold (I) in Dealuminated H-Mordenite Zeolite, Langmuir, 17, 5678-5684 (2001).*
Written Opinion of the International Searching Authority for PCT/GB2009/002293, mailed Feb. 24, 2010.
Bahn, a. et al., "Specifity of Sites within Eight-Membered Ring Zeolite Channels for Carbonylation of Methyls to Acetyls", J. Am Chem. Soc., vol. 129, (2007), pp. 4919-4924.
Donovan, A.W.O. et al., "Effect of acid and steam treatment of Na- and H-mordenite on their structural, acidic and catalytic properties", Microporous Materials, vol. 5, (1995), pp. 185-202.

* cited by examiner

*Primary Examiner* — Paul A Zucker
*Assistant Examiner* — Mark Luderer
(74) *Attorney, Agent, or Firm* — Nixon & Vanderhye P.C.

(57) ABSTRACT

Method for the selective dealumination of the aluminum within the 12-membered ring channels of a zeolite of structure type MOR. The method includes the steps of (i) loading a MOR zeolite in the hydrogen or ammonium form with a univalent metal to obtain a metal loaded zeolite; and (ii) treating the metal loaded zeolite with steam at a temperature of at least 400° C. to obtain a metal loaded dealuminated zeolite.

14 Claims, 3 Drawing Sheets

SELECTIVE DEALUMINATION OF MOR TYPE ZEOLITES

This application is the U.S. national phase of International Application No. PCT/GB2009/002293, filed 29 Sep. 2009, which designated the U.S., and claims priority to EP Application No. 08253328.2, filed 13 Oct. 2008, the entire contents of each of which are hereby incorporated by reference.

This invention relates to a process for the selective dealumination of zeolites of structure type MOR, and, in particular to the dealumination of mordenites. The invention also relates to the use of dealuminated MOR zeolites as catalysts in the carbonylation of methanol and/or dimethyl ether with carbon monoxide to produce at least one of acetic acid and methyl acetate.

BACKGROUND OF THE INVENTION

Classically, zeolites are defined as aluminosilicates with open 3-dimensional framework structures composed of corner-sharing $TO_4$ tetrahedra, where T is aluminium or silicon. Cations that balance the charge of the anionic framework are loosely associated with the framework oxygens and the remaining pore colume is filled with water molecules. The non-framework cations are generally exchangeable and the water molecules removable. The tetrahedra are connected forming rings and cages including pores and pore networks that extend throughout the zeolite crystal. The rings of a zeolite are usually formed of 8, 10, or 12 tetrahedral units, although zeolites having larger rings have been synthesised. The framework type of a zeolite is assigned a three letter framework type code by the International Zeolite Association (IZA). For example, MOR is assigned to zeolitic materials which have the framework structure of mordenite. Descriptions of all the framework types that have been assigned codes by IZA are included in the Database of Zeolite Structures (www.iza-structure.org). Zeolite structures are also defined in the 'Atlas of Zeolite Structure Types', W M Meier, D H Olson and Ch Baerlocher, $6^{th}$ revised edition, 2007, Elsevier.

Zeolites having framework type code MOR have 12-membered ring main channels with intersecting 8-membered ring channels (side-pockets). Mordenites have framework type code MOR.

Zeolites, in general, both natural and synthetic, have been demonstrated to have catalytic properties for various types of chemical processes. In particular, mordenites have been shown to catalyse the carbonylation of methanol and/or dimethyl ether with carbon monoxide to produce acetic acid and/or methyl acetate. For example, the carbonylation of methanol with carbon monoxide in the presence of a copper, nickel, iridium, rhodium or cobalt loaded mordenite catalyst to produce acetic acid, is described, for example in EP-A-0 596 632. In WO 2006/121778 there is described a process for the production of a lower alkyl ester of a lower aliphatic carboxylic acid by carbonylating under substantially anhydrous conditions a lower alkyl ether with carbon monoxide in the presence of a mordenite or ferrierite zeolite catalyst. In WO 2005/105720 there is described a process for the preparation of carboxylic acids and derivatives thereof in the presence of mordenite which has framework elements in addition to aluminium and silicon and which has also been loaded with copper, nickel, iridium, rhodium or cobalt.

The article 'Specificity of Sites within Eight-Membered Ring Zeolite Channels for Carbonylation of Methyls to Acetyls' Bhan A et al, J. Am. Chem. Soc. 2007, 129, 4919-4924, discusses the reactivity of $CH_3$ groups located within eight-membered ring channels in mordenite and ferrierite in carbonylation reactions.

U.S. Pat. No. 3,551,353 describes a process for the dealumination of mordenite by contacting steam and mineral acid in alternate steps. The dealuminised mordenite is disclosed to be active for hydrocarbon conversion reactions such as cracking.

U.S. Pat. No. 5,238,677 describes a process for the dealumination of a zeolite having the structure of mordenite by contacting the zeolite with a dicarboxylic acid and steaming.

U.S. Pat. No. 4,654,316 describes a process for selective surface dealumination of zeolites by sequential ion-exchange and calcination to improve catalyst selectivity in hydrocarbon conversion reactions.

It is highly desirable in carbonylation processes to improve catalyst performance. Performance measures include product selectivity, product yield, catalyst stability and lifetime.

In carbonylation processes which use mordenite as catalyst, the target products are acetic acid and/or methyl acetate. The production of hydrocarbons in these carbonylation processes is highly undesirable. Hydrocarbons can form a layer of coke on the catalyst which leads to catalyst deactivation. Without wishing to be bound by theory, it is believed that, in carbonylation processes, the reactions leading to the formation of hydrocarbon by-products take place in the 12-membered ring channels of a MOR zeolite whilst the reactions leading to the formation of carbonylation products is believed to take place in the 8-membered ring channels. Thus, it would be highly desirable to be able to preferentially remove aluminium from the 12-membered ring channels of a MOR zeolite, thereby leading to a catalyst having improved performance in carbonylation processes.

SUMMARY OF THE INVENTION

It has now been found that selective dealumination of the aluminium within the 12-membered ring channels of a MOR type zeolite can be successfully accomplished by sequential loading of the zeolite with a univalent metal followed by treating with steam.

Accordingly, the present invention provides a method for the selective dealumination of a zeolite of structure type MOR, which method comprises
  (i) loading the MOR zeolite with a univalent metal to obtain a metal loaded zeolite; and
  (ii) treating the metal loaded zeolite with steam at a temperature of at least 400° C. to obtain a metal loaded dealuminated zeolite.

Mordenites are available from commercial sources, generally in the Na, $NH_4$ form or H-form. The $NH_4$ form can be converted to the acid (H-form) by known techniques, such as calcination at high temperature. The Na form can be converted to the hydrogen form (H-form) by converting first to an $NH_4$ form by ion exchange with ammonium salts such as ammonium nitrate. Alternatively, mordenites may be synthesised using known techniques. The preparation of mordenite from aqueous inorganic compositions is well known and there are several recipes in the literature for making mordenite such as the method described in U.S. Pat. No. 4,205,052.

Suitably, the MOR zeolite for use in the method of the present invention has a silica:alumina molar ratio of at least 10, typically in the range 10 to 90:1, for example 10 to 40:1.

The first step in the method of the present invention is to load the MOR zeolite with a univalent metal. The univalent metal may be, for example, a metal belonging to Group 1 or Group 11 of the Periodic Table of Elements. The Group 1 metals are lithium, sodium, potassium, rubidium, cesium and francium. Of these, lithium, sodium and potassium are preferred, especially preferred is sodium. The Group 11 metals are silver, copper and gold. Silver is a preferred Group 11 metal.

Techniques for loading metals onto zeolites are well known, and include, for example, impregnation and ion-exchange methods. In the method of the present invention, the univalent metal may be loaded onto the MOR zeolite by either an impregnation or an ion-exchange method.

Typically, in an impregnation technique, a metal is loaded onto a zeolite by mixing the ammonium or hydrogen form of the zeolite with a metal salt solution to form a slurry. The slurry is concentrated to recover a wet solid metal loaded zeolite, which is thereafter dried.

As an alternative to impregnation, ion-exchange can be used, wherein the zeolite is contacted with a solution of a univalent metal salt such that the zeolite is at or above its level of incipient wetness. The solution is filtered to recover a solid metal loaded zeolite which is washed, with, for example, deionised water and thereafter dried.

The loading of a MOR zeolite with a univalent metal results in the univalent metal preferentially residing in the Brønsted acid sites of the 8-membered ring channels of the zeolite. The term 'Brønsted acid site' as used throughout this specification, means an acid site in a ring channel of a MOR zeolite which is either in the hydrogen form or in the ammonium form.

The amount of the univalent metal to be loaded onto the zeolite will be dependent upon the amount of aluminium desired to be removed from the zeolite. It has been found that where the MOR zeolite is to be used as a catalyst for carbonylation reactions, it is desirable to remove aluminium from the 12-membered ring channels but not from the 8-membered ring channels thereby maximising acetyl product formation and minimising hydrocarbon formation. Thus, preferably, the amount of univalent metal to be loaded onto a hydrogen or ammonium form of a MOR zeolite is an amount sufficient to exchange all or substantially all of the Brønsted acid sites in the 8-membered ring channels of the MOR zeolite with the univalent metal cations but not the Brønsted acid sites in the 12-membered ring channels.

The number of Brønsted acid sites in the 8-membered ring channels is equivalent to the amount of aluminium present in the 8-membered ring channels. The amount of aluminium in the 8-membered ring channels can be determined by a combination of conventional analytical methods. Aluminium ICP (inductively coupled plasma) spectroscopy can be used to determine the total amount of aluminium present in the MOR zeolite and high vacuum infra-red analysis can be used to determine the ratio of the amount of aluminium present in the 8- and 12-membered ring channels. The exact ratio of Brønsted acid sites in the 8- and 12-membered ring channels of a MOR zeolite will depend upon the method by which the zeolite was prepared. Typically, it has been found that for mordenite, the ratio of Brønsted acid sites in the 8-membered ring channels to the 12-membered ring channels is 50:50. Thus, to exchange all of the Brønsted acid sites in the 8-membered ring channels the amount of univalent metal loaded onto mordenite should be equivalent to 50 mol % of the total amount of aluminium present in the mordenite. However, if desired, greater or lesser amounts of univalent metal may be loaded. If greater than 50 mol % of univalent metal is loaded, Brønsted acid sites in the 12-membered ring channels will be exchanged by the metal cations. If less than 50 mol % of univalent metal is loaded, not all of the Brønsted acid sites in the 8-membered ring channels will be exchanged by the metal cations. For subsequent use as a carbonylation catalyst, it is preferred that all of the Brønsted acid sites in the 8-membered ring channels of the MOR zeolite are exchanged by the univalent metal cations. The extent of exchange of the Brønsted acid sites in the 8 and 12-membered ring channels by the univalent metal cations can be determined by infra-red spectroscopy.

In step (ii) of the present invention, the MOR zeolite loaded with univalent metal cations is subjected to a steaming procedure. Optionally, prior to steaming, the metal loaded zeolite may be calcined. It is preferred to calcine metal loaded zeolites which have been prepared by impregnation of the ammonium form of the MOR zeolite with the univalent metal. Calcination of such zeolites will remove ammonia and partially convert the zeolite to its hydrogen form. Where the metal loaded zeolite is calcined, the calcination may be carried out at high temperature, such as at least 400° C., for several hours in air or an inert gas.

The univalent metal loaded zeolite is exposed to a steaming procedure consisting of contacting the zeolite with steam. The steam may be used as a mixture with an inert gas, such as nitrogen. The concentration of steam present in the mixture is not critical but is suitably in the range 5 to 99 mol %.

The steaming is conducted at a temperature of at least 400° C. The steaming procedure may be carried out at any temperature in excess of 400° C. provided that the temperature used does not cause significant deformation of the MOR zeolite crystal structure. Typically, steaming may be conducted at a temperature in the range 400 to 600° C. For mordenite, it is preferred to carry out the steaming at a temperature in the range 400 to 600° C., such as in the range 500 to 600° C.

The steaming may be conducted at atmospheric or elevated pressure.

The steaming may be carried out as a fixed bed or as a fluidised bed process.

Steaming is carried out for as long as required to provide the desired dealumination. Suitably, the steam treatment time is at least about 1 hour, preferably at least 3 hours.

The treatment with steam effects the removal of aluminium. The extent to which dealumination occurs will depend on the temperature at which steaming is carried out, the duration of the steaming, the concentration of steam the MOR zeolite is exposed to and the amount of univalent metal loaded onto the zeolite. Preferably, all or substantially all of the aluminium is removed from the 12-membered ring channels. However, lesser amounts of aluminium may be removed from the 12-membered ring channels whilst still providing an improved carbonylation catalyst. The amount of aluminium removed from the zeolite can be determined by high vacuum infra-red spectroscopy.

The selective dealuminated MOR zeolites obtained by the method of the present invention have increased silica:alumina ratios from the starting zeolites. Generally, the silica:alumina ratio of the dealuminated zeolite is increased by an amount in the range 5 to 100%. The silica:alumina ratio of the dealuminated MOR zeolite can be determined by Inductively Coupled Plasma (ICP) analysis.

The method of the present invention allows improved carbonylation catalysts to be prepared. The carbonylation catalysts are prepared by converting the metal loaded dealuminated MOR zeolite of step (ii) to its hydrogen form. The hydrogen form may be optionally exchanged with one or more metal(s). The catalysts so prepared have been found to provide improved activity in carbonylation processes than conventional mordenites.

Accordingly, the present invention provides a MOR zeolite having improved carbonylation catalytic activity, said MOR zeolite obtained by
 (i) loading a MOR zeolite with a univalent metal to obtain a metal loaded zeolite;
 (ii) treating the metal loaded zeolite with steam at a temperature of at least 400° C. to obtain a metal loaded dealuminated zeolite; and
 (iii) converting the metal loaded dealuminated zeolite to the hydrogen form of the dealuminated zeolite.

Additionally, the present invention provides a process for the production of at least one of acetic acid and methyl acetate which process comprises the carbonylation of at least one carbonylatable reactant selected from methanol and dimethyl ether with carbon monoxide in the presence of a zeolite catalyst, which zeolite is a dealuminated zeolite of structure type MOR has been obtained by
 (i) loading a MOR zeolite with a univalent metal to obtain a metal loaded zeolite;
 (ii) treating the metal loaded zeolite with steam at a temperature of at least 400° C. to obtain a metal loaded dealuminated zeolite; and
 (iii) converting the metal loaded dealuminated zeolite to the hydrogen form of the dealuminated zeolite.

The present invention also provides for the use of a zeolite catalyst to provide improved catalytic activity in the carbonylation of methanol and/or dimethyl ether with carbon monoxide to produce methyl acetate and/or acetic acid, wherein said improved catalytic activity is obtained by preparing the catalyst according to steps (i) to (iii) hereinabove described.

Conversion of the metal loaded dealuminated zeolite to the hydrogen form may be achieved by any suitable technique. Suitable techniques include converting the dealuminated zeolite into its ammonium form, followed by calcination to remove ammonia. The ammonium form of the zeolite may be obtained by contacting the zeolite with an aqueous solution of an ammonium salt, such as ammonium nitrate. After contacting with the ammonium salt, the dealuminated zeolite may be washed, one or more times, with deionised water to remove univalent metal which has been exchanged for $NH_4^+$, any excess $NH_4^+$ and any extra-framework aluminium species. After washing, the zeolite may be subjected to a drying step to remove water. After being dried, the ammonium form of the dealuminated zeolite is calcined.

Alternatively, the metal loaded dealuminated zeolite may be treated with a mineral acid, such as hydrochloric or nitric acid, at a pH below 7. Treatment with a mineral acid, converts the metal loaded zeolite into its hydrogen form and also removes extra framework aluminium, generated during the steaming, from within the zeolite channels. The steamed zeolite is added to a solution of the mineral acid, typically 0.5 to 1.0 molar, but generally not exceeding 2.0 molar. The duration of the acid wash is not critical, but preferably, is sufficient to remove essentially all of the extra framework aluminium from within the zeolite channels. A duration of 1 to 5 hours is generally sufficient but the exact duration will depend on the temperature at which the acid wash is carried'out. The acid wash may be carried out at ambient temperature or at elevated temperature such as 50 to 100° C., for example 50 to 80° C. The acid treated zeolite is filtered and washed with deionised water to neutral pH.

The hydrogen form of the dealuminated MOR zeolite may be optionally ion-exchanged or otherwise loaded with one or more metals such as copper, silver, gold, nickel, iridium, rhodium, platinum, palladium or cobalt.

Such metals may be loaded onto the hydrogen form of the dealuminated MOR zeolite by any suitable technique such as by ion-exchange and impregnation as hereinabove described.

The metal loading on the dealuminated MOR zeolite may be expressed in terms of the fractional loading of the metal as gram atoms of metal per gram atom of aluminium in the zeolite. The metal loading can also be expressed as a mole percentage loading relative to aluminium in the zeolite through the relationship:

mol % Metal=(gram atoms Metal/gram atoms aluminium)×100

Suitably, the metal loading may be in the range of 1 to 200 mol % relative to aluminium in the zeolite.

Prior to use as a catalyst in the carbonylation process, the dealuminated mordenite in its hydrogen form or optionally loaded with one or more metals such as copper, silver, gold, nickel, iridium, rhodium, platinum, palladium or cobalt may be calcined. Calcination is suitably carried out by heating at elevated temperature, for example 400-550° C., for at least one hour in air or an inert gas.

The carbonylation process of the present invention employs at least one of methanol and dimethyl ether as the carbonylatable reactant. Dimethyl ether may be generated in-situ, for example, from dimethyl carbonate.

Where the carbonylatable reactant is dimethyl ether, the carbonylation process is typically carried by passing the dimethyl ether, carbon monoxide and optionally hydrogen through a fixed or fluidised bed of dealuminated MOR zeolite catalyst, such as dealuminated mordenite, maintained at the required temperature, such as in the range 150 to 350° C., for example, in the range 250 to 350° C.

The carbonylation of dimethyl ether to methyl acetate does not generate water in-situ. Water has also been found to inhibit the carbonylation of dimethyl ether to form methyl acetate. Thus, where dimethyl ether is the carbonylatable reactant, the carbonylation process is conducted as an anhydrous process, that is water is kept as low as is feasible. To accomplish this dimethyl ether, carbon monoxide and hydrogen (if used) and the MOR catalyst are preferably dried prior to use in the carbonylation process. However, small amounts of water may be tolerated without adversely affecting the formation of methyl acetate. Suitably, the dimethyl ether feed may contain up to 2.5 wt % water.

The carbonylation of dimethyl ether produces, as the primary product of the process, methyl acetate but small amounts of acetic acid may also be produced. The methyl acetate produced by the process of the present invention can be removed in the form of a vapour and thereafter condensed to a liquid.

The methyl acetate may be recovered from the product stream of the carbonylation process and sold as such or it may be forwarded to other chemical processes. Where the methyl acetate is recovered from the product stream, some or all of it may be hydrolysed to form acetic acid. Alternatively, the entire carbonylation product stream, comprising mainly methyl acetate, some acetic acid and unconverted dimethyl ether, may be passed to a hydrolysis step and acetic acid separated therefrom. The hydrolysis step may be carried out by known techniques such as reactive distillation in the presence of an acid catalyst.

Where the carbonylatable reactant is methanol, the carbonylation process is typically carried out by passing the methanol, carbon monoxide and optionally hydrogen through a fixed or fluidised bed of the dealuminated MOR zeolite catalyst, such as dealuminated mordenite, maintained at the required temperature, such as in the range 250 to 400° C., for example, 275 to 350° C.

The carbonylation of methanol, produces as the predominant product, acetic acid, but some methyl acetate may also be present, depending on the degree of conversion of methanol.

The carbon monoxide may be substantially pure carbon monoxide, for example, carbon monoxide typically provided by suppliers of industrial gases, or it may contain impurities that do not interfere with the conversion of the dimethyl ether to methyl acetate, such as nitrogen, helium, argon, methane and/or carbon dioxide.

The carbonylation process of the present invention may be carried out in the presence of hydrogen. The hydrogen may be fed as a separate stream to the carbonylation reactor or it may be fed in combination with, for example carbon monoxide. Mixtures of hydrogen and carbon monoxide are commercially produced by the steam reforming of hydrocarbons and by the partial oxidation of hydrocarbons. Such mixtures are commonly referred to as synthesis gas. Synthesis gas comprises mainly carbon monoxide and hydrogen but may also contain smaller quantities of carbon dioxide.

Suitably, the molar ratio of carbon monoxide:hydrogen may be in the range 1:3 to 15:1, such as 1:1 to 10:1, for example, 1:1 to 4:1. The molar ratio of carbon monoxide to carbonylatable reactant is suitably in the range 1:1 to 99:1, such as 2:1 to 60:1.

The carbonylation process of the present invention may be carried out at a total pressure in the range 1 to 100 barg. Suitably, the pressure may be in the range of 10 to 80 barg.

Where hydrogen is employed, the hydrogen partial pressure is suitably in the range 0.1 to 50 barg.

The carbon monoxide partial pressure should be sufficient to permit the production of the carbonylation product, but is suitably in the range 0.1 to 50 barg.

The Gas Hourly Space Velocity (GHSV) is suitably in the range 500 to 40,000 $h^{-1}$, such as 2000 to 20,000 $h^{-1}$.

Preferably, the carbonylation process of the present invention is carried out substantially in the absence of halides, such as iodide. By the term 'substantially' is meant that the halide, for example, the iodide content of the reactant gases (dimethyl ether and carbon dioxide) and catalyst is less than 500 ppm, preferably less than 100 ppm.

The carbonylation process may be operated as either a continuous or a batch process, preferably as a continuous process.

BRIEF DESCRIPTION OF THE DRAWINGS

The invention is further described with reference to the accompanying drawings, in which.

The invention is now illustrated with reference to the following Examples.

Example 1

Preparation of Catalyst A—Dealuminated H-mordenite

This example illustrates the preparation of a dealuminated H-mordenite catalyst by (i) loading a mordenite with sodium cations to obtain Na-mordenite, (ii) steaming the Na-mordenite to obtain a dealuminated Na-mordenite and (iii) converting the dealuminated Na-mordenite to a dealuminated H-mordenite by treating with mineral acid.

Infra-red spectra of the mordenite CBV21A ($NH_4$—mordenite having a silica:alumina ratio of 20 ex Zeolyst International) and other samples generated in this Example were obtained from a Bruker Vector 33 infra-red spectrometer. The spectra were measured in the 3800-3500 $cm^{-1}$ region on a 13 mm diameter self-supporting disc (~20 mg) held within a Specac High Temperature High Pressure cell (P/N 5850) in transmission mode and operating at 5 to $8\times10^{-2}$ mbar pressure. The disc was heated to a temperature of 420° C. at 5° C./min and maintained at this temperature for 16 hours to remove water and any other volatile components. The temperature of the disc was then reduced to 150° C. and a spectrum recorded. Each spectrum was obtained by averaging 64 scans collected at 2 $cm^{-1}$ resolution. An empty High Temperature High Pressure cell at a temperature of 150° C. and a pressure of $8\times10^{-2}$ mbar was used as the spectroscopic background.

Figure 1:
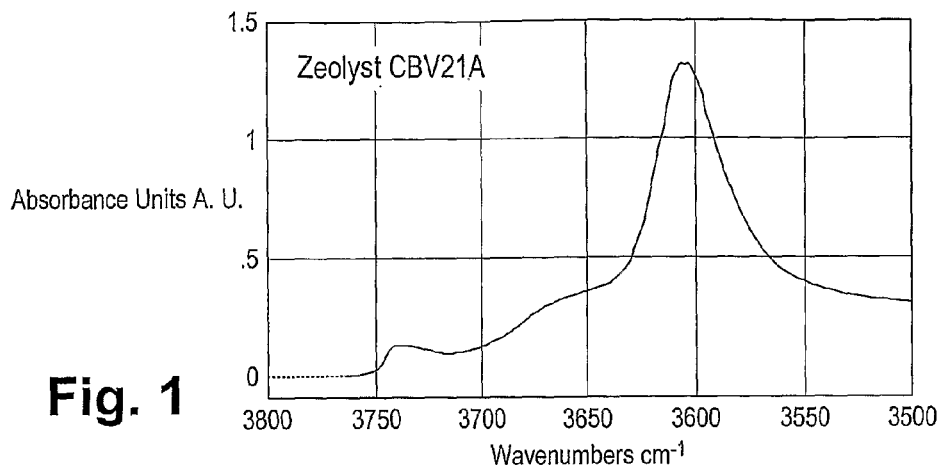
FIG. 1 is the infra-red spectrum of CBV21A mordenite.

The infra-red spectrum of CBV21A mordenite is shown in FIG. 1. Deconvolution of the spectrum from FIG. 1 showed O—H-stretches at ~3610 $cm^{-1}$ for the Brønsted acid sites in the 12-membered ring channels and at ~3590 $cm^{-1}$ for the Brønsted acid sites in the 8-membered ring channels.

50 g of CBV21A mordenite was mixed with 3.02 g of $NaNO_3$ (35.5 mmol) in 120 ml deionised water and stirred for 16 hours at room temperature. The mixture was then concentrated in vacuo until solid. The solid was dried in an oven at a temperature of 110° C. for 20 hours and then calcined at 500° C. for 3 hours in static air. The calcined solid (Na-mordenite) was analysed by high vacuum infra-red spectroscopy. The infra-red spectrum of the Na-mordenite, showed O—H stretches at ~3610 $cm^{-1}$ but no O—H stretches at ~3590 $cm^{-1}$ indicating that sodium cations had replaced all of the Brønsted acid sites in the 8-membered ring channels but none of the Brønsted acid sites in the 12-membered rings.

Figure 2:
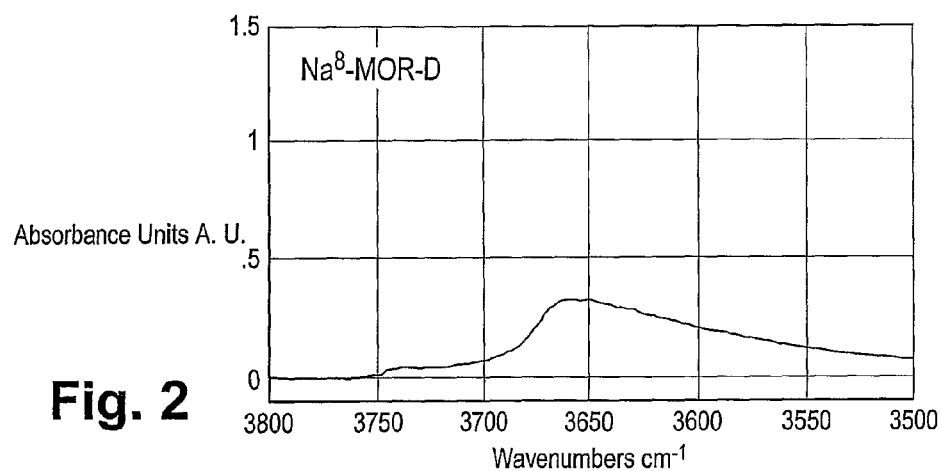
FIG. 2 is the infra-red spectrum of dealuminated Na-mordenite.

8 g of the Na-mordenite was loaded and secured in a quartz tube between two pieces of glass wool. The quartz tube was packed with 15-20 cm of Raschig glass rings, to act as a pre-heat material. A nitrogen flow of 80 $cm^3$ $min^{-1}$ was introduced and the quartz tube was heated to 500° C. using the temperature program: ambient temperature to 90° C. over 10 min, held at 90° C. for 30 min, heated to 110° C. over 10 min, held at 110° C. for 30 min, then heated to 500° C. over 60 minutes and held at that temperature for 4 hours. At 500° C. a flow of deionised water was introduced for 4 hours at the rate of 1 ml $min^{-1}$ into the top of the quartz reactor via a needle. The steam concentration was 94 mol %. After 4 hours the flow of water was ceased. The quartz tube was cooled to ambient temperature under a nitrogen atmosphere for 12 hours. The cooled solid (dealuminated Na-mordenite) was analysed by high vacuum infra-red spectroscopy. The infra-red spectrum of the dealuminated Na-mordenite is shown in FIG. 2. No O—H stretches were found to occur at ~3610 $cm^{-1}$ confirming that aluminium had been removed from the 12-membered ring channels.

Figure 3:
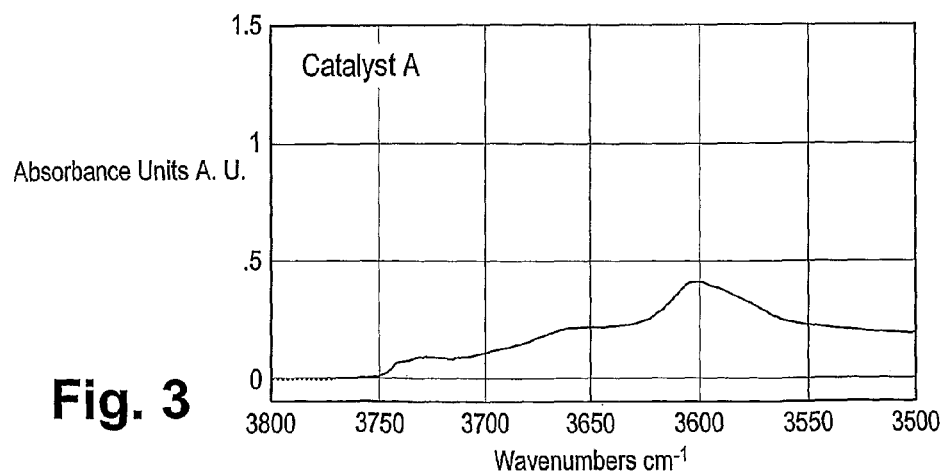
FIG. 3 is the infra-red spectrum of dealuminated H-mordenite.

8 g of the dealuminated Na-mordenite was treated with an aqueous solution of HCl (80 ml, 1M) at 80° C. for 1 hour. The solution was filtered to obtain solid dealuminated H-mordenite. The solid was washed with copious amounts of deionised water to remove all trace of chloride ions from the solid. The solid was then dried in an oven at a temperature of 110° C. for 20 hours. The solid was analysed by high vacuum infra-red spectroscopy. The infra-red spectrum obtained is shown in FIG. 3. The presence of O—H stretches at ~3590 cm$^{-1}$ indicated that the sodium cations had been replaced by H$^+$ confirming that the solid obtained was dealuminated H-mordenite.

Example 2

Preparation of Catalyst D—H-mordenite (not in Accordance with the Invention)

This example illustrates the preparation of a non-dealuminated H-mordenite catalyst. 10 g of NH$_4$-mordenite of silica:alumina ratio of 20 (CBV21A Zeolyst International) was calcined at 500° C. for 3 hours in static air to obtain H-mordenite.

Example 3

Carbonylation of Dimethyl Ether Using Catalysts A and D

This example illustrates the use of Catalysts A and D for the carbonylation of dimethyl ether.

Figure 4:
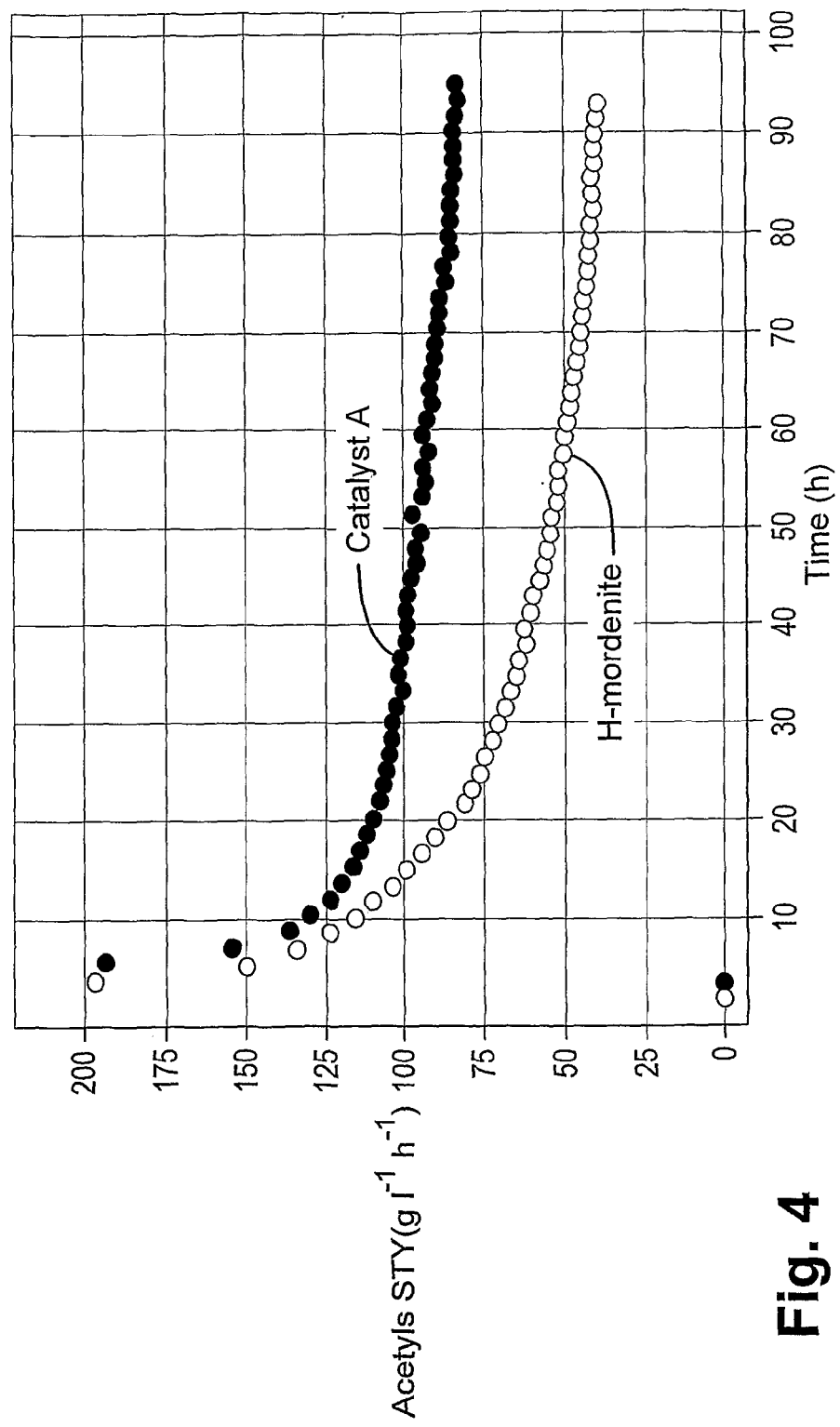
FIG. 4 is depicts the space time yield (STY) to acetyls products versus time on stream for the carbonylation of dimethyl ether using Catalysts A and D.

A Hastelloy reactor tube was packed with 0.6 ml of catalyst and a pre-bed of gamma alumina (0.2 g). Prior to use, each catalyst had been pressed (32 mm die in a specac press at 12 tonnes) and sieved to a particle size in the range 250 to 500 microns. The portion of the reactor tube containing the catalyst was heated by means of an electrical heating jacket. The reactor and heating jacket were themselves mounted in a heated cabinet which maintained the temperature of the pre-bed. The reactor was heated at atmospheric pressure under a flow of nitrogen to 130° C. in the heated cabinet. Once at temperature, the feed gas was changed to 80 mole % carbon monoxide and 20 mole % hydrogen and the reactor system was pressurised to 20 barg. The gas mixture was fed to the reactor from a gas header through a mass flow controller at a gas flow rate of 5000 per hour. The reactor was heated to 300° C. at a ramp rate of 3° C. per minute using the electrical heating jacket. Once at temperature these conditions were maintained for two hours, after which the carbonylation reaction was started by introducing dimethyl carbonate at a flow rate sufficient to achieve a gas feed comprising 76 mole % carbon monoxide, 19 mole % hydrogen and 5 mole % dimethyl ether. A constant flow of reaction off-gases was taken from the high pressure side of the reactor system through a needle valve, let down to atmospheric pressure while maintaining a temperature of at least 130° C. and passed to a gas chromatograph for analysis. The reactor effluent comprising methyl acetate and acetic acid was passed to a gas chromatograph for analysis. The space time yield (STY) of acetyls products was calculated as the molar equivalent weight of acetic acid corresponding to the sum of the methyl acetate and acetic acid produced expressed as grams of acetic acid per hour per liter of catalyst. FIG. 4 depicts the space time yield (STY) to acetyls products versus time on stream for the carbonylation of dimethyl ether using Catalysts A and D.

The data in FIG. 4 clearly shows that the dealuminated Catalyst A is more effective than the non-dealuminated Catalyst D in converting dimethyl ether to the carbonylation products, methyl acetate and acetic acid.

Example 4

Preparation of Catalyst B—Calcined Dealuminated Ag-mordenite 10 g Catalyst A was stirred into a solution of 1.36 g AgNO$_3$ (8 mmol) in 100 ml deionised water at 80° C. for 2 hours to obtain a silver loaded dealuminated mordenite, which was washed with approximately 1.5 liters of deionised water, dried at a temperature of 110° C. for 20 hours and then calcined at 500° C. for 3 hours in static air.

Example 5

Preparation of Catalyst C—Non-calcined Dealuminated Ag-mordenite

Example 4 was repeated except that the calcination step was not performed.

Example 6

Preparation of Catalyst E—Calcined Non-dealuminated Ag-mordenite (Not in Accordance with the Invention)

20 g of NH$_4$-mordenite of silica:alumina ratio 20 (CBV21A Zeolyst International) was mixed with a solution of 2.72 g AgNO$_3$ (16 mmol, solution concentration of 80 mmol l$^{-1}$) in 200 ml deionised water and stirred in the absence of light for 2 hours at 80° C. The solution was then filtered to obtain solid Ag-mordenite. The solid was washed with copious amounts of deionised water (~1.5 liters per 10 g of solid) in the absence of light. The wet Ag-mordenite was dried at a temperature of 110° C. for 20 hours and then calcined for 3 hours at 500° C. in static air.

Example 7

Carbonylation of Dimethyl Ether Using Catalysts B, C and E

Figure 5:
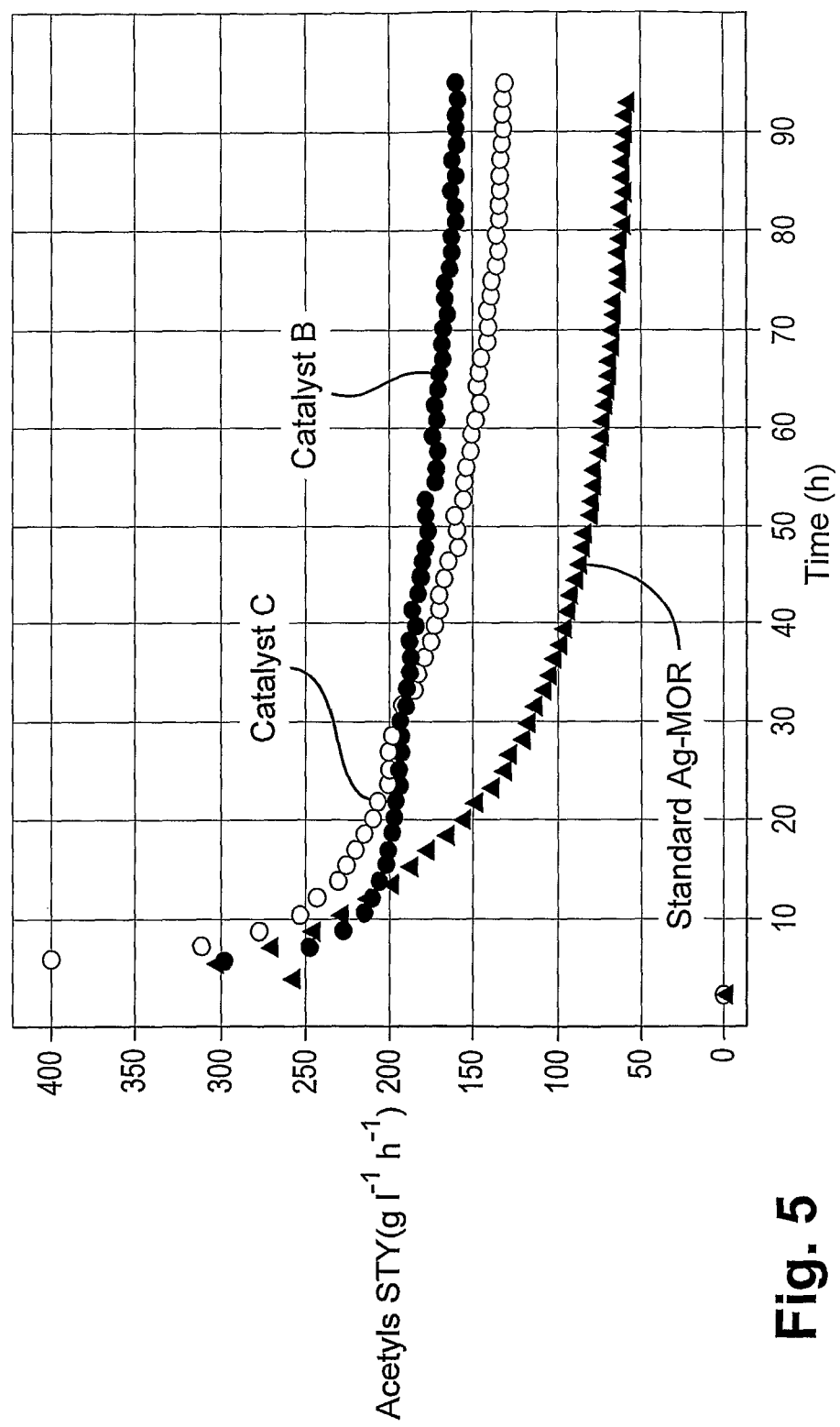
FIG. 5 depicts the space time yield (STY) to acetyls products versus time on stream for the carbonylation of dimethyl ether using Catalysts B, C and E.

Carbonylation of dimethyl ether was carried out according to the procedure of Example 3 using Catalysts B, C and E. The results of the carbonylation reactions are shown in FIG. 5. FIG. 5 depicts the space time yield (STY) to acetyls products versus time on stream for the carbonylation of dimethyl ether using Catalysts B, C and E.

As can be seen from FIG. 5, the dealuminated Ag-mordenite catalysts of the invention (Catalysts B and C) provide superior performance in the carbonylation reaction compared to the non-dealuminated Ag-mordenite (Catalyst E).

The invention claimed is:
1. A method for the selective dealumination of the aluminum within the 12-membered ring channels of a zeolite of structure type MOR, which method comprises the steps:
   (i) loading a MOR zeolite in the hydrogen or aluminum form with a univalent metal to obtain a metal loaded zeolite, wherein the MOR zeolite is loaded with the univalent metal to exchange all or substantially all of the Brønsted acid sites in the 8-membered ring channels but not the Brønsted acid sites in the 12-membered ring channels;

(ii) treating the metal loaded zeolite with steam at a temperature of at least 400° C. to obtain a metal loaded dealuminated zeolite.

2. A method according to claim 1 wherein the univalent metal is a metal belonging to Group 1 or Group 11 of the Periodic Table of Elements.

3. A method according to claim 2 wherein the univalent metal is sodium or silver.

4. A method according to claim 2 wherein the MOR zeolite is mordenite and mordenite is loaded with the univalent metal in an amount equivalent to 50 mol % of the total amount of aluminium present in the mordenite.

5. A method according to claim 1 wherein prior to step (ii) the zeolite is calcined.

6. A method according to claim 1 wherein the metal loaded zeolite is treated with steam to effect the removal of all or substantially all of the aluminium from its 12-membered ring channels.

7. A method according to claim 1 wherein the metal loaded dealuminated MOR zeolite of step (ii) is converted to the hydrogen form of the dealuminated MOR zeolite.

8. A method according to claim 7 wherein the metal loaded dealuminated zeolite is converted to the hydrogen form by converting the dealuminated zeolite into its ammonium form and then calcining the ammonium form of the dealuminated zeolite.

9. A method according to claim 7 wherein the metal loaded dealuminated zeolite is converted to the hydrogen form by treatment with a mineral acid at a pH of below 7.

10. A method according to claim 7 wherein the hydrogen form of the dealuminated zeolite is ion-exchanged or otherwise loaded with one or more metals selected from copper, silver, gold, nickel, iridium, rhodium, platinum, palladium and cobalt.

11. A method according to claim 1 wherein the metal loaded dealuminated zeolite is calcined.

12. A MOR zeolite having improved carbonylation catalytic activity, said MOR zeolite obtained by:
(i) loading a MOR zeolite in the hydrogen or ammonium form with a univalent metal to obtain a metal loaded zeolite, wherein the MOR zeolite is loaded with the univalent metal to exchange all or substantially all of the Brønsted acid sites in the 8-membered ring channels but not the Brønsted acid sites in the 12-membered ring channels;
(ii) treating the metal loaded zeolite with steam at a temperature of at least 400° C. to selectively dealuminate the aluminum within the 12-membered ring channels of the MOR zeolite to obtain a metal loaded dealuminated zeolite; and
(iii) converting the metal loaded dealuminated zeolite to the hydrogen form of the dealuminated zeolite.

13. A process for the production of at least one of acetic acid and methyl acetate by the carbonylation of at least one carbonylatable reactant selected from methanol, dimethyl ether and dimethyl carbonate with carbon monoxide in the presence of a zeolite catalyst which zeolite is a dealuminated zeolite of structure type MOR and obtained by the method of claim 7.

14. A process according to claim 13 wherein the carbonylation produces a product stream comprising methyl acetate and the methyl acetate is recovered and hydrolysed to acetic acid or the product stream is hydrolysed and acetic acid recovered therefrom.

* * * * *